United States Patent [19]

Chance

[11] Patent Number: 4,972,331
[45] Date of Patent: Nov. 20, 1990

[54] PHASE MODULATED SPECTROPHOTOMETRY

[75] Inventor: Britton Chance, Philadelphia, Pa.
[73] Assignee: Nim, Inc., Philadelphia, Pa.
[21] Appl. No.: 307,066
[22] Filed: Feb. 6, 1989
[51] Int. Cl.$^5$ .......................... G06F 15/00; A61B 5/00
[52] U.S. Cl. .................................... 364/550; 128/633; 364/413.09
[58] Field of Search .................. 364/413.09, 497, 554, 364/575, 525, 550; 356/318, 319, 39, 40, 346, 333; 250/213 VT, 281; 455/611, 612; 128/633, 634, 637

[56] References Cited

U.S. PATENT DOCUMENTS

| | | | |
|---|---|---|---|
| 3,638,640 | 2/1972 | Shaw | 128/633 |
| 4,138,727 | 2/1979 | Mantz | 356/346 |
| 4,510,938 | 4/1985 | Jöbsis | 128/633 |
| 4,576,173 | 3/1986 | Parker et al. | 128/633 |
| 4,800,495 | 1/1989 | Smith | 364/413.09 |
| 4,800,885 | 1/1989 | Johnson | 128/633 |
| 4,807,630 | 2/1989 | Malinouskas | 128/633 |
| 4,819,646 | 4/1989 | Cheung et al. | 128/633 |
| 4,819,752 | 4/1989 | Zelin | 128/633 |
| 4,824,242 | 4/1989 | Frick et al. | 128/633 |
| 4,827,938 | 5/1989 | Parker | 128/634 |
| 4,832,484 | 5/1989 | Aoyagi et al. | 128/633 |

OTHER PUBLICATIONS

Chance et al., Time-Resolved Spectroscopy of Hemoglobin and Myoglobin in Resting and Ischemic Muscle, Analytical Biochemistry 174, pp. 698–707, (1988).

Primary Examiner—Kevin J. Teska
Attorney, Agent, or Firm—Woodcock Washburn Kurtz Mackiewicz & Norris

[57] ABSTRACT

The present invention to provides methods and apparatus for studying photon migration using signal modulation techniques such as time, frequency and phase modulation. The photon migration data may then be converted, using the principles of time-resolved spectroscopy, to determine the concentration of an absorptive constituent in a scattering medium, such as the concentration of hemoglobin in a brain of other tissue. The methods and apparatus of the present invention provide as a specific embodiment, a dual wavelength phase modulation system which allows the clinical application of time resolved spectroscopy in a commerically feasible embodiment.

16 Claims, 3 Drawing Sheets

PHASE MODULATED SPECTROPHOTOMETRY

CROSS-REFERENCE TO RELATED APPLICATIONS

This application is related to co-pending applications, Ser. No. 266,166, filed Nov. 2, 1988, in the name of Britton Chance, entitled, "Optical Coupling System for Use in Monitoring Oxygenation State Within Living Tissue", which is hereby incorporated by reference as if fully set forth herein; Ser. No. 266,019, filed Nov. 2, 1988, in the name of Britton Chance, entitled, "A User-Wearable Hemoglobinometer For Measuring the Metabolic Condition of a Subject", which is hereby incorporated by reference as if fully set forth herein; and Ser. No. 287,847, filed Dec. 21, 1988, in the name of Britton Chance, entitled, "Methods and Apparatus For Determining the Concentration of a Tissue Pigment Of Known Absorbance, In Vivo, Using the Decay Characteristics of Scattered Electromagnetic Radiation", which is hereby incorporated by reference as if fully set forth herein.

BACKGROUND OF THE INVENTION

The application of the basic dual wavelength principle to detect hemoglobin and myoglobin changes in tissue began with the work of G.A. Millikan in his studies of the cat soleus muscle, and the work of Millikan and Pappenheimer who detected hemoglobin deoxygenation in the human ear lobe. Multiwavelength instruments have been developed; these instruments use either a multiwavelength laser diode light source or a time shared filter technique, in which high precision is sought through various algorithms which deconvolute background signals, oxidized and reduced cytochrome signals, and oxy- and deoxyhemoglobin signals. Such instruments are oxy-complex and often have difficulty obtaining light sources with wavelengths appropriate to the algorithms that have been developed, or they have such low light levels that photon counting is necessary. They are generally in the price range of $80,000 and have produced much experimental data in the literature on neonates and adults. The basic problem of such methods is that the optical pathlength is not known ab initio but is calculated by reference to animal models where the hemoglobin can be removed and cytochrome directly studied. Transferability of such data from the animal model to the human is one difficulty that had to be overcome prior to the invention of time-resolved spectroscopy, where the pathlength is measured directly. See U.S. Pat. Application Ser. No. 266,166, filed Nov. 2, 1988, "Optical Coupling System for Use in Monitoring Oxygenation State Within Living Tissue," fully referenced above.

Continuous wave spectroscopy (CWS) of tissue hemoglobin has the demonstrated advantages of great simplicity and sensitivity, as well as affording an "early warning" of tissue hypoxia. The application of picosecond-pulse time-resolved spectroscopy (TRS) to tissue in order to determine optical pathlengths, quantify the changes in hemoglobin concentration, and determine the actual concentration values of hemoglobin and cytochrome has great applicability to clinical studies of tissue hypoxia. Moreover, time-resolved spectroscopy used in conjunction with continuous light spectrophotometry offers a means of calibrating the optical pathlength which photons travel as they migrate through tissue. While trend indication can be of great value in many situations, the capability to quantify hemoglobin concentration for both continuous and pulsed light techniques greatly extends their applicability to clinical studies. See U.S Pat. Application Ser. No. 266,166, filed Nov. 2, 1988, "Optical Coupling System for Use in Monitoring Oxygenation State Within Living Tissue"; and U.S. Application Ser. No. 287,847, filed Dec. 21, 1988, "Methods and Apparatus For Determining the Concentration of a Tissue Pigment Of Known Absorbance, In Vivo, Using the Decay Characteristics of Scattered Electromagnetic Radiation", both of which are fully referenced above.

SUMMARY OF THE INVENTION

It has now been found that the principles of dual wavelength spectrophotometry may be applied to time-resolved spectrophotometry choosing a carrier frequency at a value in which the time characteristic is compatible with the time delay of photon migration from input to output through a scattering medium.

The present invention provides methods and apparatus whereby a modulated waveform is transmitted to a scattering medium and detected after migration therethrough. The detected waveform will have been altered and may thus be compared to the initial waveform. For example, a waveform is phase shifted by the delay in migration through the scattering medium. Thus, in a preferred embodiment, the phase of the waveform is modulated and the phase shift is detected. The difference in phase shift between two waveforms of emitted electromagnetic radiation having different, known wavelengths can then be processed to determine the concentration of an absorptive constituent such as hemoglobin.

It is an object of the present invention to provide methods and apparatus for studying photon migration using signal modulation techniques such as time, frequency and phase modulation. It is a specific object of the present invention to provide methods and apparatus whereby phase modulated spectrophotometry (PMS) may be utilized in conjunction with continuous wave spectrometry (CWS) to determine the critical value of an absorptive pigment such as hemoglobin, at the point the $PCr/P_I$ ratio begins to decrease. It is another object of the present invention to provide as a specific embodiment, a dual wavelength phase modulation system which will allow the clinical application of the advantages of time resolved spectroscopy in an economical and commercially feasible embodiment.

DETAILED DESCRIPTION

Figure 1A:
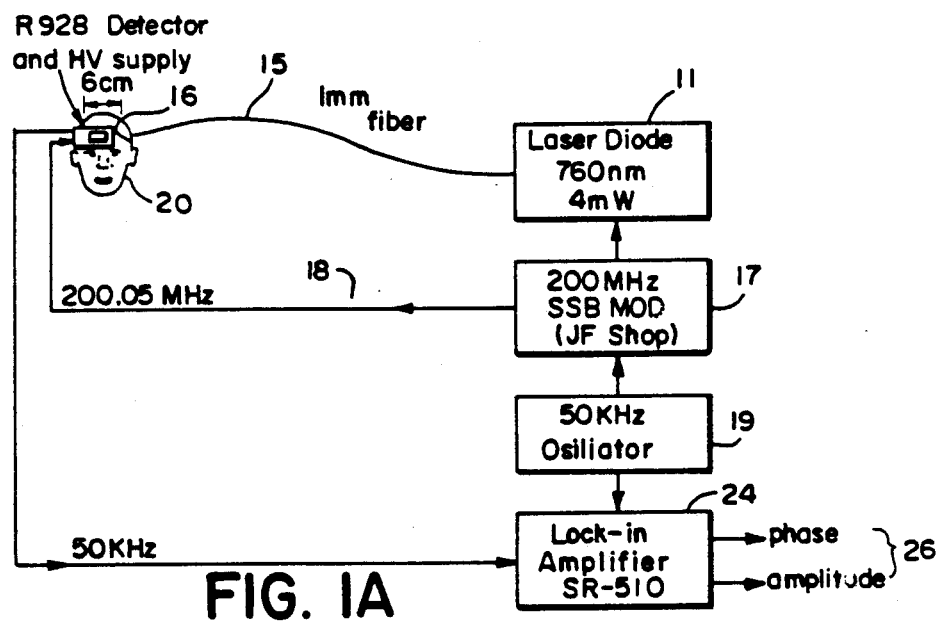
FIG. 1A illustrates a simplified single wavelength phase modulated spectrophotometer made in accordance with the present invention.

The time, frequency, or phase of a signal may be modulated. Phase modulation appears to be a convenient implementation of the time-released spectroscopy (TRS) technique discussed above. In FIG. 1A, a single wavelength spectrophotometer using the principle of phase modulation is shown. In this embodiment, a frequency generator 17, operating at 200 MHz, excites a 4mW laser diode 11, which emits light at a wavelength of 760 nm. The light is conducted to the subject 20 via optic fiber 15. After the light has migrated through the tissue, it is detected. Preferably this detector is comprised of a photomultiplier tube and its associated voltage supply 16; one such device is the Hamamatsu R928.

The frequency generator 17 also receives an input from a 50 kHz oscillator 19, transmitting a 200.05 MHz reference waveform, which is input into the detector 16. Accordingly, the output waveform 22 from the detector 16 is at a carrier frequency equal to the difference, i.e., 50 kHz. The waveform 22 from the detector 16 and a reference waveform from the oscillator 19 are fed into a phase and amplitude detector 24. In this embodiment, the phase and amplitude detector 24 is a lock-in amplifier. The output of the lock in amplifier are signals representative of the phase shift and amplitude of the detected signal. These signals are then processed and related to the relative concentration of an absorbing constituent, such as hemoglobin.

Figure 1:
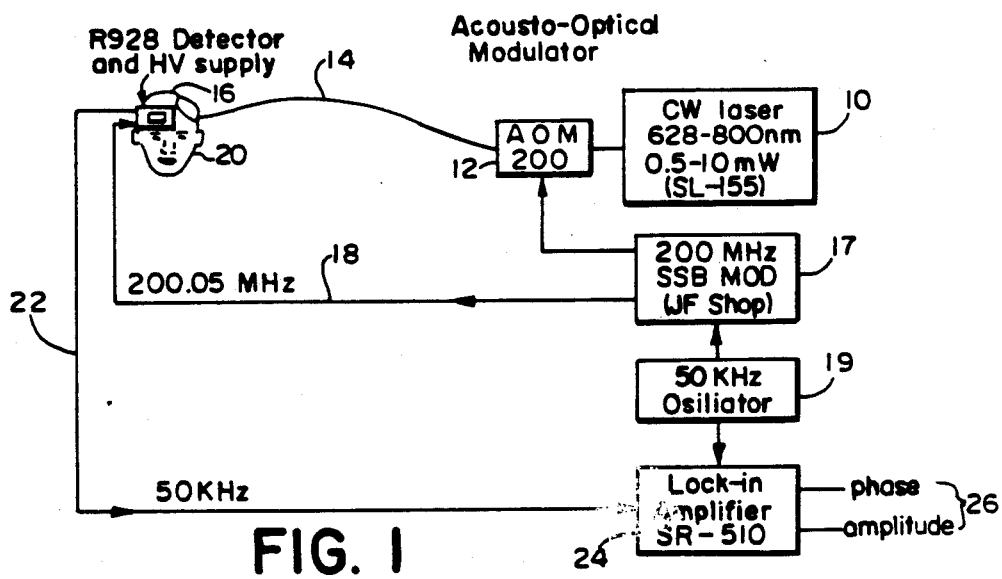
FIG. 1 is a block diagram of another embodiment of a single wavelength phase modulated spectrophotometer made in accordance with the present invention.

In the embodiment of FIG. 1, a helium-neon laser light source 10 is connected to a wide band acousto-optical modulator 12 operating at 200 MHz. The acousto-optical modulator 12 frequency modulates the light emitted by the laser 10. The light is conducted via a fiber optic light guide 14 to the forehead of the subject 20 as shown, or other region to be studied. Signals about 3-6 cm from the location of the input waveform are received by a detector 16, for example a Hamamatsu R928. The dynodes are modulated by a 200.050 MHz signal 18 so that a 50 kHz hetrodyne signal 22 will be obtained and can be fed into a lock-in amplifier 24, such as a PAR SR510. As above the reference frequency for the lock-in amplifier is obtained from the 50 Hz difference between the two frequencies. The phase shift between the transmitted and detected waveforms is measured with high precision and the output waveforms, shown at 26, are plotted as an analog signal on a strip chart recorder to allow the user to follow the variations in the propagation of light through the brain or other tissue. A logarithmic conversion of the signal is then obtained. The result is linearly related to the change in concentration of an absorptive pigment, such as hemoglobin.

Figure 2:
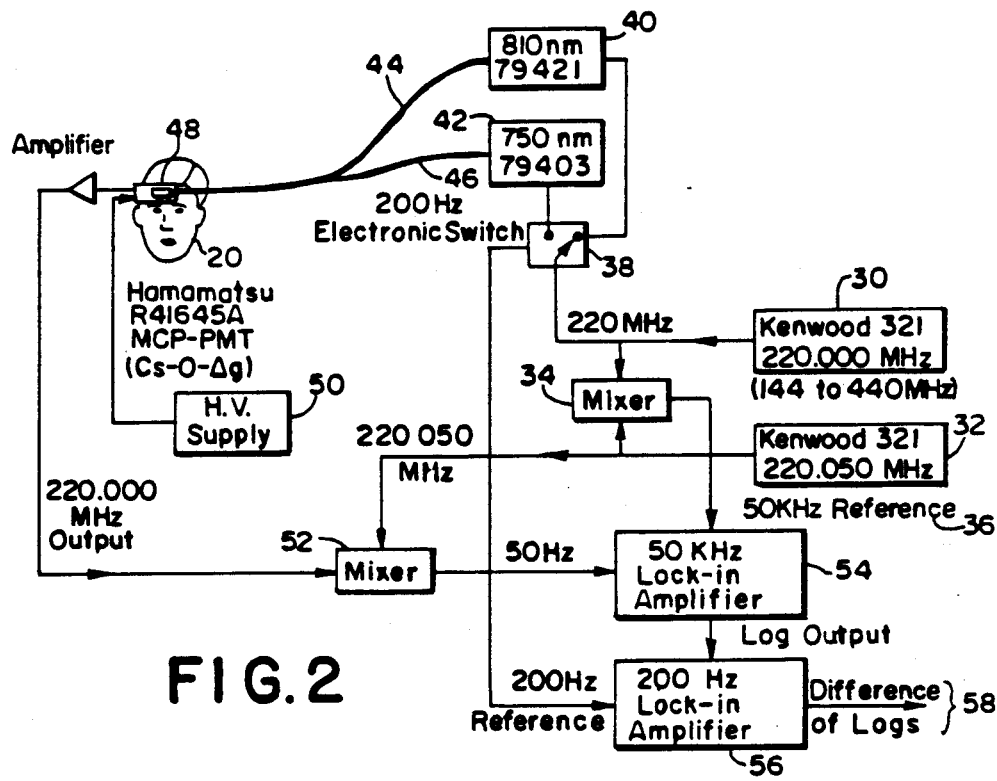
FIG. 2 is a block diagram of another embodiment of a phase modulated spectrophotometer made in accordance with the present invention.

Referring to FIG. 2, there is shown a block diagram of a simplified embodiment of a dual wavelength phase modulation spectrophotometer made in accordance with the present invention. Unlike the single wavelength system of FIG. 1A, this embodiment allows the determination of the concentration of an absorptive constituent on an absolute basis. The embodiment of FIG. 2 is similar to that depicted in FIG. 1A, except that light is transmitted to the subject at two discrete wavelengths.

FIG. 2 illustrates a dual wavelength embodiment of the apparatus of the present invention. In this embodiment, the laser diode light is amplitude modulated and the phase shift caused by photon migration is measured by an optical detector, a mixer, and a phase detector.

The dual frequency time sharing system is comprised of stable oscillators 30,32, such as Kenwood Model #321 for 220 Hz; the oscillator system preferably used can generate waveforms from 144 to 440 MHz (Kenwood TM721A). Continuous variation of the frequency is possible, although, as will be understood by one of ordinary skill, the three frequencies mentioned, 144, 220 and 440 MHz, are adequate for the purposes of initial studies and other applications. The oscillators 30,32 are set 50 Hz apart and the difference frequency is detected by a mixer 34 to obtain a reference phase signal 36, as shown. A 200 Hz electronic switch 38 alternately excites laser diodes 40,42, nominally operating at between about 750-60 nm and 800-10 nm, to emit 220 MHz modulated light which is conducted by fiber optic guides 44,46, preferably about 3 mm in diameter, to the surface of the head of the subject 20, or other region to be examined.

In order to achieve satisfactory operation at 220 MHz, it has been found that the most cost effective detector 48 for this purpose is Hamamatsu R928. A more advantageous device, however, is the Hamamatsu R1645u, which is a microchannel plate tube having 120 picosecond transit time spread, and a high gain; that is, a two-stage microchannel plate photomultiplier 48. This tube, which is capable of current amplification of $5 \times 10^5$ (57 dB) is similar to those used for pulsed time measurements in time resolved spectroscopy (TRS) studies, and is considered to be ideal for these purposes. See, Chance et al., "Time-Resolved Spectroscopy of Hemoglobin and Myoglobin in Resting and Ischemic Muscle," Analytical Biochemistry 174, 698-707 (1988). tube 48 is connected to a high voltage supply 50 which has an output of about 3400 volts, in order to ensure high gain. The photomultiplier tube 48 can be connected to the brain or other tissue area by the fiber optic guides 44,46 or may be directly connected and placed in a housing isolated from ground potential, as illustrated.

As above, the detector 48 is attached to the subject 20 and is connected to a mixer 52, which down converts the 220 MHz output of the detector 48 to a 50 kHz signal by mixing with a 220.050 MHz signal from the oscillator 32. A lock-in amplifier 54 determines the phase of the exiting waveform. The lock-in amplifier 54 also obtains the logarithm of the signal. This signal is then fed to a second phase detector/lock-in amplifier 56 which determines the difference between the signals at each of the two wavelengths, this signal 58 is directly proportional to the concentration of an absorptive pigment, such as hemoglobin. This embodiment may be used on neonate, as well as adult brains.

Figure 3:
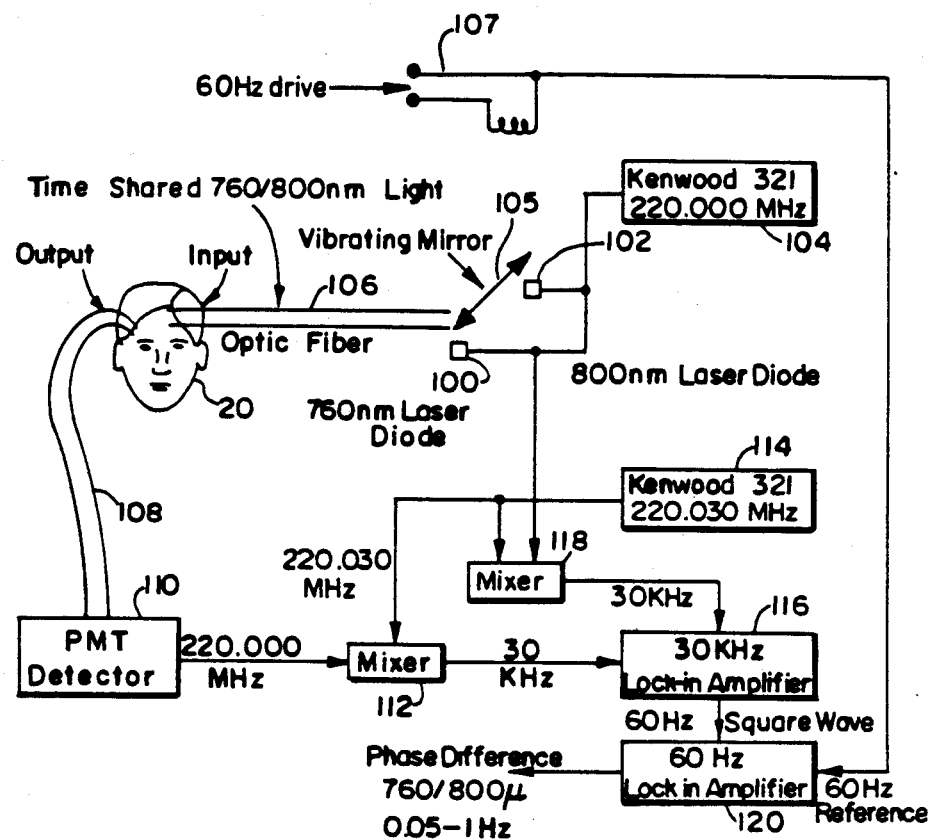
FIG. 3 is a block diagram of the preferred embodiment of the spectrophotometer of the present invention.

A preferred embodiment of a time-shared, dual wavelength laser diode phase modulation spectrophotometer is illustrated in FIG. 3. In this embodiment, a pair of laser diodes 100,102 are excited in parallel by a stable frequency generator 104 (Kenwood 321) at 220 MHz. Each of the diodes 102,104 generates electromagnetic radiation of a different wavelength, preferably 760 nm and 800 nm. The electromagnetic radiation is time shared by a vibrating mirror 105, which illuminates a single fiber optics probe at a modulating frequency, preferably about 60 Hz. The synchronization of the motion of the mirror 105 and the 60 Hz phase detector 120 (explained below) is accomplished using an electrical coupling of the reference voltage in the 60 Hz lock-in amplifier 120. Thus, electromagnetic radiation at each wavelength is synchronized between emission and detection.

One of ordinary skill will note that the spectrophotometer of FIG. 3 differs from the embodiment depicted in FIG. 2 in that the latter embodiment uses a carrier modulation system to code the excitation power of one laser from another, while the embodiment of FIG. 3 continuously switches between the output light from two lasers excited at the same frequency.

The time shared 760/800 nm light is applied to the subject 20 via an optic fiber 106. Several centimeters away, an output probe 108, preferably comprising a second fiber of relatively large area will pick up the light which has migrated through the subject and illuminates a photo detector 110, which is a suitable photomultiplier tube (Hamamatsu 928) or a microchannel plate detector (Hamamatsu R1645u). The light collected is phase shifted from input oscillations by the time delay in photon migration between input and output.

A second oscillator 114 which generates a 220.030 MHz waveform is connected to a mixer 112. The 220.000 MHz output of the detector 110 is also connected to the mixer. As a result, the phase modulation frequency is downshifted to 30 kHz, which is a convenient frequency for lock-in detection. This signal is input to a phase detector 116, which is preferably a lock-in amplifier. A second input to the phase detector 116 is obtained by connecting an output from the 220.000 MHz oscillator 104 and the 220.030 MHz oscillator 114 to a mixer 118 to obtain an unshifted 30 kHz signal which is used as a phase reference. Thus, the lock-in amplifier 116 operates with a reference phase obtained directly from the frequency generators 104,114 and a phase modulated input obtained by photon migration through the subject 20.

The phase of the signal output will vary between the phase due to light propagation at 800 nm and the phase due to light propagation at 760 nm. The output of the lock-in amplifier 116 is thus a 60 Hz waveform, the amplitude of which bears the phase information at the two wavelengths. The output of the phase difference detector 116 then is connected to the same waveform as that which drives the 60 Hz vibrating mirror 105. The output of the phase detector may be obtained by using switch contacts on the vibrating reed modulation which alternatively connects opposite phases of the 60 Hz waveform to the integrating network, each one at the peak of the waveform of the output phase detector. The output is put into a differential amplifier to record the difference of the amplitude of the two parts of the 60 Hz waveform, corresponding to the 760 nm and 800 nm phase shift. This phase difference output is suitably filtered from 0.05–1 Hz and provides a running time record of the changes in hemoglobin concentration by dual wavelength time-resolved spectroscopy.

The advantage of the system illustrated by FIG. 3 is that it affords a single light guide input to the subject operated from two laser diodes which are continuously operated at the same oscillator frequency. Thus, spurious phase differences in frequencies associated with excitation are minimized. That is, no differential phase shift is expected between the 760 nm and 800 nm signals. Thus, the 30 kHz difference signal would represent the true phase delay between these two wavelengths. Moreover, phase noise in this region would be minimized by the differential detector 116. The photomultiplier tube detector 110 can be of any adequately fast type, since the mixing function is separated from the detector. The lock-in amplifier technique obtained to derive the difference of the phase and amplitude of the two signals has the highest signal to noise ratio possible for this type of equipment.

The principles of time-shared dual wavelength spectrophotometry, together with lock-in technology, follows the principles employed in dual wavelength spectrophotometry generally. However, the present invention provides a vastly improved device, since the carrier frequency of 220.000 MHz is sufficiently fast to measure photon migration times between input and output with a characteristic time of about 5 nanoseconds to be observed. Therefore, the sensitivity of the system disclosed is high, approximately 70° per nanosecond or 3° per centimeter change of pathlength, as observed in experimental models.

The application of the principles of dual wavelength spectrophotometry to time-resolved spectrophotometry involves the choice of a carrier frequency at a value in which the time characteristic is compatible with the time delay of photon migration from input to output. The device disclosed achieves the result of precisely measuring the absorbance changes in photon migration, over a specified distance, e.g., over approximately one meter, as contrasted, to the continuous light method in which photon migration is measured over all possible path lengths. A path length of approximately one meter is preferably selected in order to ensure exploration of all parts of the brain for brain bleeding studies. Obviously, higher frequencies would select smaller portions of the brain which are more localized to the input-output configuration.

For a multiple-scattering medium such as human tissue, the only known method for determining the path length of transmitted photons is the measurement of the time of flight and of the refractive index, from which the distance travelled may be calculated. Since this path length in the brain is on the order of centimeters, the transit time is on the order of nanoseconds or less. A direct measurement of such periods in this time domain has several fundamental drawbacks. As the required time resolution becomes finer, the detection bandwidth must increase; signal power at best remains constant, while noise power increases proportionally with the increasing bandwidth. For sources such as laser diodes, where average output power for both pulsed and continuous operation are nearly the same, signal power typically declines when the pulse width is reduced. Since the time between probe pulses must be long enough for the returning light to decay to approximately zero, the duty cycle of the pulse train is typically low; this implies low average signal power or the use of high peak power, which may endanger the skin covering the tissue being studied. Finally, both the expense and difficulty of constructing suitable electronic circuits is considerably greater for pulsed than for continuous-wave systems. As an alternative to time-domain measurement, a CW system may be employed with phase measurement taking the place of time intensity, a simple calculation based on measurement of the phase shift between probe and return light at a single frequency yields the characteristic decay time. Such a system has the advantages of narrowband modulation and detection and high average power in the probe signal, yielding a considerable advantage in signal-to-noise ratio and therefore in data acquisition time. There is a considerable body of literature on this technique of time measurement, particularly as applied to radar, time standards, and spectroscopy. Perhaps the most relevant to this application is the literature on the phase-resolved measurement of fluorescent decay kinetics.

Figure 4:
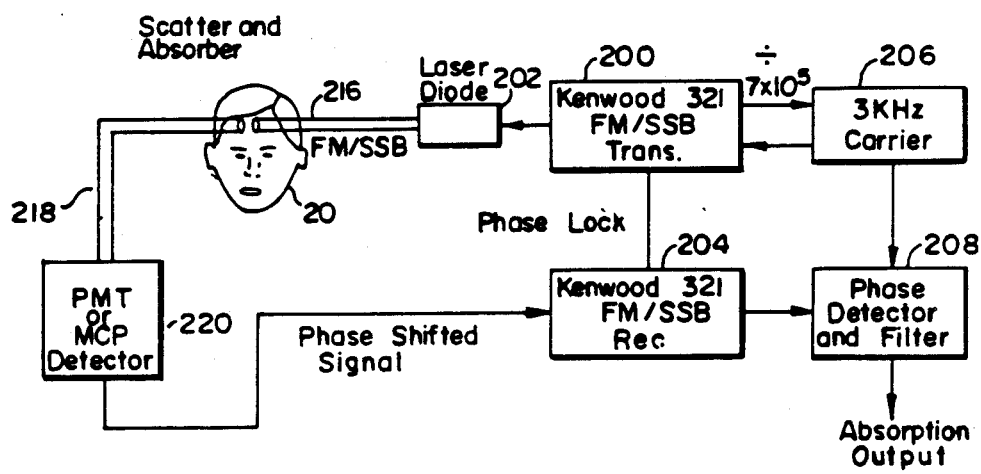
FIG. 4 is a block diagram of an alternate embodiment of the spectrophotometer of the present invention.

Another alternate embodiment of the apparatus of the present invention is depicted in FIG. 4. This system relies more upon communications technology rather than NMR technology, and is essentially a single sideband system where the sidebands are displaced in proportion to the modulation frequency shift required. This design places more reliance upon the existing radio frequency transmitter/receivers which, at prices of about $300 per frequency for transmit/receive, is a significant advantage.

A block diagram of a system as described directly above is shown in FIG. 4. In this embodiment, a first standard communications transmitter-receiver (transceiver) 200, operating at 220 MHz, is used in the transmit mode to generate a waveform which excites a laser diode 202. The transceiver 200 is used in the single side band (SSB) mode to provide SSB modulation at 3 kHz. This carrier signal is fed back to the transceiver 200 and into a phase detector/filter 208, which also receives an input from a second transceiver 204. As in the previous embodiments, the laser diode 202 emits light which is conducted to the subject 20 via optic fibers 216.

The SSB modulated signal is phase shifted by the delay in migration through the brain. The light is scattered and absorbed as it migrates through the subject 20 and is received by an optical coupler/fiber assembly 218. The received light is then transmitted to a detector 220, either of the photomultiplier tube or the microchannel plate type, both of which are discussed above in reference to other embodiments.

The output of the detector 220 is coupled to the RF input to the second transceiver 204, i.e., the transceiver is used in the receive SSB mode and a phase shifted 3 kHz tone is obtained and connected to the phase detector filter 208. The output is a 3 kHz phase shifted signal which is input to the second SSB transceiver 204. In order to ensure phase coherence, the first transceiver 200 and the second transceiver 204 form a phase locked loop. The 3 kHz carrier waveform is also locked to 220 MHz by frequency dividers 206, thereby locking the 220 MHz and the 3 kHz phases and allowing the phase shift to be determined with high precision. As seen in FIG. 4, an output of the transmitter oscillator 200 is frequency divided by about $7 \times 10^5$, to yield a 3 kHz signal. The output of the phase detector/filter 208 is thus related to the phase shift and, accordingly, is representative of the absorption within the subject.

The carrier frequency is initially chosen to be 220 MHz; this is sufficiently high to give a detectable phase shift for decay times of a few nanoseconds, but low enough to be within the bandwidth of a number of commercially-available active mixers. Although diodering mixers are readily available up to 36 GHz, they have significantly less dynamic range than active (transistor bridge or linear multiplier) designs; a large dynamic range is crucial for this type of spectrophotometer system. A heterodyne system is chosen to allow multiple optical wavelengths to be transmitted and detected in parallel on individual subcarrier frequencies, and to allow phase detection to be carried out within the frequency range of commercial phase sensitive detectors, i.e., "lock-in amplifiers". These devices have a superb noise figure, linearity, dynamic range, and phase and amplitude accuracy; their performance is very much superior to any phase detector operating directly at the RF carrier frequency. Generation of the reference signals for the lock-in amplifiers by frequency division from the master RF oscillator provides adequate phase coherence of all subcarriers and all demodulated signals with respect to the carrier; no phase calibration between wavelengths is required. Frequency generation by division also provides minimum possible phase noise for a given master oscillator. Should additional carrier frequencies be required, such as for the measurement of multi-exponential decays, the only changes required in this design would be the addition of a one-by-N RF switch and additional RF oscillators.

Laser diodes are chosen over thermal sources, for their much higher radiance, ease of coupling to optical fiber, narrow output spectrum and wavelength stability, long life, and ease of modulation at RF frequencies. In order to maximize the signal-to-noise ratio of the system, and to avoid problems of intermodulation distortion due to laser nonlinearities, single-sideband suppressed-carrier modulation is used. The intermediate frequencies are chosen within the range of 10 to 100 KHz; they must be high enough to allow a realizable Q of the single side band filters, but low enough to be within the range of low-cost commercial lock-in amplifiers.

The heat sinks of the lasers are preferably temperature-controlled using Peltier coolers and feedback control. Temperature control is necessary in order to stabilize the wavelength of the lasers, and to allow sufficient tuning of the output wavelength to cover the tolerance (approx. $\pm 10$ nm) of commercial diodes. However, it should be noted that post-demodulation detection of phase shift substantially eliminates this consideration, since neither constant wavelength nor amplitude are required.

The optical system consists of one optical isolator per laser, lens assemblies for coupling the laser light into the optical fibers, a fiber bundle(s) for transmitting the light to and from the subject, a fiber-subject coupler on the distal end of the bundle(s), and a light detector assembly.

The isolators are necessary in order to prevent optical feedback into the laser cavity due to reflections from the optics or subject; such feedback, even at levels as low as $-60$ dB, are well known to cause both amplitude and phase noise in laser sources.

The fibers chosen for fabrication of the bundles must have sufficiently small dispersion that the phase uncertainty introduced at the nominal 100 MHz modulation frequency is much smaller than the phase shifts of interest. At the same time, the maximum possible core diameter and numerical aperture are desired. This simplifies and makes more robust the laser-fiber coupling, and greatly increases the return light signal collected from the subject, which greatly increases the return light signal collected from the subject, which is approximately a Lambertian radiator. For this reason, single-mode fibers are ruled out, despite their extraordinary bandwidth-length products. For multimode fiber, only modal dispersion is significant for the sources, lengths, and bandwidths considered here; we therefore disregard waveguide and material dispersion. Considering first a step-index fiber, simple ray optics will show that it is numerical aperture, and not core size, that determines modal dispersion. For an allowable time uncertainty of 100 picoseconds, and a total step-index fiber length of two meters, a numerical aperture of approximately 0.17 or less would be required; all commercial step-index multimode fibers have a much larger numerical aperture. For an ideal graded-index multimode fiber, however, modal dispersion for meridional rays is zero, from Fermat's principle, and actual bandwidth-length products in commercial graded-index fibers exceed 100 MHz-km at the wavelength of interest for this study. We therefore choose a graded-index fiber with 100 micron core size, 0.3 numerical aperture, and 100 MHz-km bandwidth-length product. This fiber is also cheap enough ($0.50/meter) to be considered for fabricating bundles.

The detection optics consist of a fiber bundle of cross-sectional area matched to the active area of the detector, an optical bandpass or comb filter to pass only the laser wavelengths and prevent detector saturation by room light, and the detector itself. Initially, a photomultiplier tube with a GaAs(Cs) photocathode will be used; this detector has a gain advantage of about thirty compared to a PMT with silicon photocathode, and about 300 compared to a silicon avalanche photodiode, not including the much smaller active area of the avalanche photodiode. However, the photomultiplier tube also has a marginal bandwidth for this application, and extraction of the signal from the middle of the dynode chain may be required, thus reducing the gain. Should the signal-to-noise ratio prove sufficient, the system may be easily modified later by substitution of an avalanche photodiode for the PMT, reducing the cost and increasing bandwidth, reliability and ruggedness. The avalanche photodiode detectors are also to be used for imaging experiments due to their smaller size and lower cost. Conversely, if greater detection bandwidth and high gain are needed simultaneously, a microchannel plate photomultiplier may be used; the disadvantages here are the much greater cost and lower photocathode sensitivity, approximately a factor of 30 compared to GaAs(Cs) available.

After a variable gain stage, the signals out of the detector are heterodyned back to the IF frequencies and fed into commercial two-phase lock-in amplifiers; one lock-in per optical wavelength (If frequency) is used. While this increases the cost, it reduces data acquisition time by a factor of about 1.41 (SQRT 2) (comparing two amplifiers to one), and avoids undesirable assumptions about the relative absorption kinetics at each wavelength.

The entire system may be controlled by an IBM-compatible portable computer, with IEEE 488, analog-digital, digital-analog, and bidirectional digital interfaces. All of the latter can be provided by two low-cost plug-in cards for the IBM. The use of the computer control has a number of significant advantages, among them the possibility of automatic operation for testing and phantom experiments, simplified reconfiguration as the system is refined, speed, accuracy, and ease of post-processing of data, in particular for statistical analysis. The choice of a portable machine greatly simplifies clinical trials of the present invention.

The technology of multiwavelength phase modulation each encoded by its own subcarrier can readily be carried out as illustrated in the preferred embodiment of FIG. 3. The output of such a system would then replace the continuous wave technology of existing systems, and at the same time, take advantage of the algorithms for decoding various states of hemoglobin and even cytochrome. The great advantage is that the optical pathlength is known and not assumed. Thus, phase modulation is a convenient implementation of the TRS technique, since it can be built to emphasize delay times on the order of 5 nanoseconds where the decay is exponential and long path migrations are involved.

What is claimed is:

1. In a scattering medium comprising one or more constituents having specific concentrations and having a quantifiable parameter associated with a particular wavelength of electromagnetic radiation, a method of determining the concentration of an absorptive constituent in the scattering medium, comprising the steps of:
   (a) generating a carrier waveform having a frequency of at least 100 MHz appropriate to propagation in the scattering medium;
   (b) generating electromagnetic radiation chosen to propagate effectively in the scattering medium and having a known wavelength;
   (c) imposing said carrier waveform upon said electromagnetic radiation to generate a modulated waveform;
   (d) coupling said modulated waveform to the scattering medium to create an altered waveform due to absorption and propagation of the modulated waveform in the scattering medium;
   (e) detecting said altered waveform, comprising said modulated waveform which has migrated through the scattering medium;
   (f) determining the optical path length through the scattering medium by measuring a variation in said quantifiable parameter associated with said electromagnetic radiation due to propagation and absorption in the scattering medium by comparing said altered waveform with a reference waveform which has not migrated through the scattering medium; and
   (g) converting said variation to a quantitative measure proportional to the concentration of said absorptive constituent in the scattering medium.

2. The method of claim 1, wherein said quantifiable parameter is time.

3. The method of claim 1, wherein said quantifiable parameter is phase.

4. The method of claim 1, wherein said quantifiable parameter is frequency.

5. The method of claim 1, further comprising the steps of:
   (a) generating second electromagnetic radiation chosen to propagate effectively in he scattering medium and having a second known wavelength;
   (b) imposing said carrier waveform upon said second electromagnetic radiation having a second known wavelength to generate a second modulated waveform;
   (c) coupling said radiation having a first wavelength and said second radiation having a second wavelength to the scattering medium in an alternating manner; and
   (d) synchronizing the detection of said altered waveform with said coupling of step (c).

6. In a scattering medium comprised of one or more constituents having specific concentrations and having a quantifiable parameter associated with a particular wavelength of electromagnetic radiation a method of determining data related to the concentration of an absorptive constituent in the scattering medium, comprising the steps of:
   (a) generating a first waveform having a first frequency of at least 200 MHz;

(b) imposing said first waveform upon at least two source of electromagnetic radiation which emit radiation of different known wavelengths;

(c) alternately coupling radiation from each of said sources to the scattering medium at an input location, said alternate coupling occurring at a reference frequency;

(d) detecting an altered waveform at an output location, said altered waveform comprising said modulated waveform which has migrated through said scattering medium;

(e) generating a second waveform having a second frequency of at least 200 MHz;

(f) mixing said altered waveform and said second waveform to create a down converted waveform;

(g) mixing said first waveform and said second waveform to create a down converted reference waveform;

(h) detecting a variation in the quantifiable parameter associated with said electromagnetic radiation due to propagation and absorption in the scattering medium by comparing said down converted waveform with said down converted reference waveform and creating an output waveform;

(i) determining the optical path length through the scattering medium by detecting the difference in said variation in a quantifiable parameter between each of said wavelengths of radiation by comparing said output waveform with said reference waveform and creating a difference output, whereby said difference output is related to the concentration of said absorbing constituent.

7. A method of analyzing a scattering medium comprised of one or more constituents having a specific concentration by determining data related to the concentration of one of said absorptive constituents, said absorptive constituent having a quantifiable parameter associated with a particular wavelength of electromagnetic radiation, comprising the steps of:

(a) generating a first waveform having a first frequency of at least 200 MHz;

(b) transmitting said first waveform to said scattering medium;

(c) detecting the phase angle of said first waveform upon its exit from said scattering medium;

(d) generating a second waveform having a second frequency of at least 200 MHz;

(e) transmitting said second waveform to said scattering medium;

(f) detecting the phase angle of said second waveform upon its exit form said scattering medium; and (g) determining the optical path length through the scattering medium by determining the phase difference between the phase angle of said first waveform and said second waveform;

whereby said first and second frequency are selected to be commensurate with the time difference between the transmission in steps (b) and (e) and the detection in steps (c) and (f), and said phase difference is related to said concentration of an absorptive constituent in a scattering medium.

8. A method of analyzing a scattering medium comprised of one or more constituents having a specific concentration by determining the concentration of an absorptive constituent in the scattering medium, said absorptive constituent having a quantifiable parameter associated with a particular wavelength of electromagnetic radiation, comprising the steps of:

(a) transmitting electromagnetic energy of two different wavelengths into said scattering medium at a carrier frequency of at least 200 MHz having a time characteristic compatible with the time delay of photon migration from input to output through said scattering medium and also related to a specified distance through said scattering medium and causing a phase shift in said electromagnetic energy;

(b) determining a difference in the phase shift of said electromagnetic energy from input to output through said scattering medium; and (c) determining the optical path length through the scattering medium and determining said concentration of an absorptive constituent by multiplying said phase shift difference by a proportionality constant, whereby the absorbance changes in said photon migration over said specified distance are measured.

9. A method of analyzing a tissue region of a subject, comprising a scattering medium of one or more constituents having a specific concentration by determining the optical path length through said scattering medium to determine the concentration of an absorptive pigment in said tissue region of a subject, comprising the steps of:

(a) generating a first waveform having a first frequency of at least 200 MHz;

(b) switching said first waveform at a switching frequency between at least two means for generating pulses of electromagnetic energy, each means capable of generating pulses of a different wavelength;

(c) transmitting a plurality of pulses of electromagnetic energy of at least two different wavelengths to an input location proximate to said tissue region;

(d) detecting the phase angle of said pulse at an exit location proximate to said tissue region;

(e) amplifying a detected signal representative of said phase angle to produce an amplified phase angle signal;

(f) generating a second waveform having a second frequency of at least 200 MHz;

(g) mixing said second waveform and said first waveform to generate a first reference waveform;

(h) mixing said second waveform and said amplified phase angle signal to generate a phase shift signal having the same frequency as said first reference waveform;

(i) comparing said first reference waveform and said phase shift signal to create phase shift data for determining optical path length;

(j) converting said phase shift data to a logarithmic scale and generating a signal representative of logarithmic phase shift data;

(k) identifying and separating data related to said pulses of different wavelengths by synchronizing said logarithmic phase shift data with said switching frequency;

(l) obtaining a difference between successive sets of said logarithmic phase shift data related to the input of pulses of different wavelengths, wherein each of said sets contains data representing each wavelength;

(m) converting said difference to the actual concentration of said absorptive constituent present by multiplying said logarithmic phase shift data by a proportionality constant.

10. Apparatus for analyzing a scattering medium comprised of one or more constituents having a specific concentration by determining the concentration of an absorptive constituent in a scattering medium, said absorptive constituent having a quantifiable parameter associated with a particular wavelength of electromagnetic radiation, comprising:
(a) oscillator means for generating a carrier waveform of a frequency of at least 200 MHz appropriate to propagation is the scattering medium;
(b) laser means for generating electromagnetic radiation having a known wavelength;
(c) means for imposing said carrier waveform upon said laser means to generate a modulated waveform;
(d) light guide means for coupling said radiation to the scattering medium;
(e) detector means for detecting an altered waveform, comprising the portion of said radiation which migrates through said scattering medium;
(f) lock-in amplifier means for determining the variation in a quantifiable parameter associated with said radiation due to propagation and absorption in the scattering medium; and
(g) means for tracking said variation as a quantitative measure related to the concentration of an absorptive constituent in the scattering medium.

11. The apparatus of claim 10, further comprising:
(h) second laser means for generating electromagnetic radiation having a second known wavelength;
(i) means for imposing said carrier waveform upon said electromagnetic radiation to generate a second modulated waveform.
(j) switching means of alternately coupling said radiation having a first wavelength and said radiation having a second wavelength to the scattering medium; and
(k) oscillator means of synchronizing the detection of said altered waveform with said alternate coupling of step (j).

12. The apparatus of claim 11, wherein said switching means is an acousto-optical modulator.

13. Apparatus for analyzing a scattering medium comprised of one or more constituents having a specific concentration by determining data related to the concentration of an absorptive constituent in the scattering medium, said absorptive constituent having a quantifiable parameter associated with a particular wavelength of electromagnetic radiation, comprising:
(a) oscillator means for generating a fist waveform having a first frequency of at least 200 MHz;
(b) means for imposing said first waveform upon at least two sources of electromagnetic radiation which emit radiation of different known wavelengths;
(c) switching means for alternately coupling radiation from each of said sources to the scattering medium at an input location, said alternate coupling occurring at a reference frequency;
(d) detector means for detecting an altered waveform at an output location, said altered waveform comprising said modulated waveform which has migrated through said scattering medium;
(e) second oscillator means for generating a second waveform having a second frequency of at least 200 MHz;
(f) means for mixing said altered waveform and said second waveform to create a down converted waveform;
(g) means for mixing said first waveform and said second waveform to create a down converted reference waveform;
(h) first lock-in amplifier means for detecting the variation in the quantifiable parameter associated with said electromagnetic radiation due to propagation and absorption in the scattering medium by comparing said down converted waveform with said down converted reference waveform and creating an output waveform;
(i) second lock-in amplifier means for detecting the difference in said variation in a quantifiable parameter between each of said wavelengths of radiation by comparing said output waveform with said reference waveform and creating a difference output, whereby said difference output is related to the concentration of said absorbing constituent.

14. The apparatus of claim 13, wherein said switching means is comprised of an electronic switch.

15. The apparatus of claim 13, wherein said switching means is comprised of:
(a) a mirror; and
(b) electromechanical drive means for vibrating said mirror.

16. Apparatus for analyzing a scattering medium comprised of one or more constituents having a specific concentration by determining the concentration of an absorptive constituent in a scattering medium, said absorptive constituent having a quantifiable parameter associated with a particular wavelength of electromagnetic radiation, comprising:
(a) first transceiver means for emitting a single side band waveform having a frequency of at least 200 MHz;
(b) means for emiting electromagnetic radiation of a specified wavelength, said means excited by said first transceiver means;
(c) means for coupling said emitting means and the scattering medium;
(d) means for collecting radiation from said emitting means after it has migrated through the scattering medium;
(e) detector means for detecting an altered waveform and providing a signal representative of said altered waveform;
(f) second transceiver means for receiving said signal and transmitting and receiving a carrier signal, thereby being in a phase locked loop with said first transceiver; and
(g) phase detector and filter means for determining the phase shift of said altered waveform and providing a signal representative of said concentration of an absorptive constituent.

* * * * *

UNITED STATES PATENT AND TRADEMARK OFFICE
CERTIFICATE OF CORRECTION

PATENT NO. : 4,972,331
DATED : November 20, 1990
INVENTOR(S) : Britton Chance It is certified that error appears in the above-identified patent and that said Letters Patent is hereby corrected as shown below:

ABSTRACT, line 1, delete "to"

Column 3, line 25 delete "lock in" and insert --lock-in--

Column 4, line 33 insert --The photomultiplier-- before the words "tube 48"

Column 8, lines 53, 54 & 55 delete "greatly increases the return light signal collected from the subject," first occurrence Column 11, line 2 delete "source" and insert --sources--

Column 13, line 35 delete "of" and insert --for--

Column 13, line 39 delete "of" and insert --for--

Column 13, line 51 delete "fist" and insert --first--

Signed and Sealed this

Thirteenth Day of October, 1992

Attest:

DOUGLAS B. COMER

*Attesting Officer*    Acting Commissioner of Patents and Trademarks